US010398307B2

(12) United States Patent
Charles

(10) Patent No.: US 10,398,307 B2
(45) Date of Patent: Sep. 3, 2019

(54) CURVATURE OF FIELD TRANSFORMATION OF OCT IMAGES DURING VITREORETINAL SURGERY

(71) Applicant: NOVARTIS AG, Basel (CH)

(72) Inventor: Steven T. Charles, Memphis, TN (US)

(73) Assignee: NOVARTIS AG, Basel (CH)

( * ) Notice: Subject to any disclaimer, the term of this patent is extended or adjusted under 35 U.S.C. 154(b) by 961 days.

(21) Appl. No.: 14/942,774

(22) Filed: Nov. 16, 2015

(65) Prior Publication Data

US 2017/0135574 A1    May 18, 2017

(51) Int. Cl.
| A61B 3/00 | (2006.01) |
| A61B 3/10 | (2006.01) |
| A61B 3/13 | (2006.01) |
| A61B 3/14 | (2006.01) |
| A61B 3/12 | (2006.01) |
| A61F 9/008 | (2006.01) |

(52) U.S. Cl.
CPC .............. *A61B 3/102* (2013.01); *A61B 3/005* (2013.01); *A61B 3/0025* (2013.01); *A61B 3/1233* (2013.01); *A61B 3/13* (2013.01); *A61B 3/145* (2013.01); *A61F 2009/00851* (2013.01)

(58) Field of Classification Search
CPC ....... A61B 3/102; A61B 3/1233; A61B 3/145; A61B 3/005; A61B 3/0025; A61B 3/13; A61F 2009/00851
See application file for complete search history.

(56) References Cited

U.S. PATENT DOCUMENTS

| 8,820,931 B2* | 9/2014 | Walsh ................. A61B 3/102 351/206 |
| 9,848,770 B2* | 12/2017 | Ehlers ................. A61B 3/102 |
| 2007/0291277 A1* | 12/2007 | Everett ............... A61B 3/102 356/497 |
| 2011/0299034 A1* | 12/2011 | Walsh ................. A61B 3/102 351/206 |
| 2015/0055093 A1* | 2/2015 | Ehlers ................. A61B 3/102 351/206 |

* cited by examiner

*Primary Examiner* — Joel Lamprecht
(74) *Attorney, Agent, or Firm* — Baker Botts L.L.P.

(57) ABSTRACT

Curvature of field transformation of OCT images during ophthalmic surgery may be performed with an OCT scanning controller that interfaces to an OCT scanner used with a surgical microscope. Real-time OCT images may be acquired by the OCT scanner, while an anamorphic transformation is applied to the OCT images to match the curvature of field for optical images viewed using the surgical microscope. The transformed OCT images may be displayed during surgery.

18 Claims, 3 Drawing Sheets

CURVATURE OF FIELD TRANSFORMATION OF OCT IMAGES DURING VITREORETINAL SURGERY

BACKGROUND

Field of the Disclosure

The present disclosure relates to ophthalmic surgery, and more specifically, to curvature of field transformation of optical coherence tomography (OCT) images during vitreoretinal surgery.

Description of the Related Art

In ophthalmology, eye surgery, or ophthalmic surgery, saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Ophthalmic surgery is performed on the eye and accessory visual structures. More specifically, vitreoretinal surgery encompasses various delicate procedures involving internal portions of the eye, such as the vitreous humor and the retina. Different vitreoretinal surgical procedures are used, sometimes with lasers, to improve visual sensory performance in the treatment of many eye diseases, including epimacular membranes, diabetic retinopathy, vitreous hemorrhage, macular hole, detached retina, and complications of cataract surgery, among others.

During vitreoretinal surgery, an ophthalmologist typically uses a surgical microscope to view the fundus through the cornea, while surgical instruments that penetrate the sclera may be introduced to perform any of a variety of different procedures. The surgical microscope provides imaging and optionally illumination of the fundus during vitreoretinal surgery. The patient typically lies supine under the surgical microscope during vitreoretinal surgery and a speculum is used to keep the eye exposed. Depending on a type of optical system used, the ophthalmologist has a given field of view of the fundus, which may vary from a narrow field of view to a wide field of view that can extend to peripheral regions of the fundus.

In addition to viewing the fundus, surgical microscopes may be equipped with optical coherence tomography (OCT) scanners to provide additional information about portions of eye tissue involved with the vitreoretinal surgery. The OCT scanner may enable imaging below a visible surface of the eye tissue during vitreoretinal surgery. However, the curvature of field of OCT images may be different than microscopy optical images viewed by the surgeon.

SUMMARY

In one aspect, a disclosed method is for performing ophthalmic surgery using curvature of field transformation of OCT images. The method may include viewing an interior portion of an eye of a patient using a surgical microscope and an ophthalmic lens generating an optical image of the interior portion of the eye. The method may also include sending a command to an OCT scanning controller coupled to the surgical microscope to generate first scan data from the interior portion of the eye. In the method, the OCT scanning controller is in communication with an OCT scanner enabled for acquiring the first scan data. In the method, the OCT scanning controller is enabled for receiving the first scan data from the OCT scanner. In the method, the first scan data are usable to generate an en face view of the interior portion of the eye. Based on optical characteristics of the surgical microscope and the ophthalmic lens, in the method, the OCT scanning controller is further enabled for applying an anamorphic transformation to the first scan data to generate second scan data that matches a curvature of field of the optical image in the en face view, and causing the second scan data to be displayed in the en face view.

In any of the disclosed embodiments of the method, the second scan data may be displayed in an ocular of the surgical microscope. In any of the disclosed embodiments of the method, the second scan data may be displayed in an external display.

In any of the disclosed embodiments of the method, the first scan data may be received as a video signal, while the second scan data may be displayed as a video signal.

In any of the disclosed embodiments of the method, applying the anamorphic transformation may further include aligning first tissue features in the first scan data with corresponding second tissue features in the optical image to determine the curvature of field. In any of the disclosed embodiments of the method, the first tissue features and the second tissue features may include retinal blood vessels.

In any of the disclosed embodiments of the method, the optical characteristics may include anamorphic distortion of an objective lens included in the surgical microscope. In any of the disclosed embodiments of the method, the optical characteristics may include anamorphic distortion of the ophthalmic lens.

In any of the disclosed embodiments, the method may include receiving an indication of desired tissue layers captured in the first scan data, and generating the second scan data to image only the desired tissue layers in the en face view.

In another aspect, a disclosed OCT scanning controller performs curvature of field transformation of OCT images during ophthalmic surgery. The OCT scanning controller may include a processor having access to memory media storing instructions executable by the processor. In the OCT scanning controller, the instructions may be executable for receiving a first command to generate first scan data from an interior portion of an eye of a patient, and sending a second command to an OCT scanner to acquire the first scan data via a surgical microscope and an ophthalmic lens. In the OCT scanning controller, the surgical microscope and the ophthalmic lens may also be used to generate an optical image of the interior portion of the eye. In the OCT scanning controller, the instructions may also be executable for receiving the first scan data from the OCT scanner. In the OCT scanning controller, the first scan data may be usable to generate an en face view of the interior portion of the eye. Based on optical characteristics of the surgical microscope and the ophthalmic lens, in the OCT scanning controller, the instructions may also be executable for applying an anamorphic transformation to the first scan data to generate second scan data that matches a curvature of field of the optical image in the en face view, and causing the second scan data to be displayed in the en face view.

In any of the disclosed embodiments of the OCT scanning controller, the instructions for causing the second scan data to be displayed in the en face view may include instructions for causing the second scan data to be displayed in an ocular of the surgical microscope.

In any of the disclosed embodiments of the OCT scanning controller, the instructions for causing the second scan data to be displayed in the en face view may include instructions for causing the second scan data to be displayed in an external display.

In any of the disclosed embodiments of the OCT scanning controller, the first scan data may be received as a video signal, while the second scan data may be displayed as a video signal.

In any of the disclosed embodiments of the OCT scanning controller, the instructions for applying the anamorphic transformation may further include instructions for aligning first tissue features in the first scan data with corresponding second tissue features in the optical image to determine the curvature of field. In any of the disclosed embodiments of the OCT scanning controller, the first tissue features and the second tissue features may include retinal blood vessels.

In any of the disclosed embodiments of the OCT scanning controller, the optical characteristics may include anamorphic distortion of an objective lens included in the surgical microscope. In any of the disclosed embodiments of the OCT scanning controller, the optical characteristics may include anamorphic distortion of the ophthalmic lens.

In any of the disclosed embodiments, the OCT scanning controller may further include instructions for receiving an indication of desired tissue layers captured in the first scan data, and generating the second scan data to image only the desired tissue layers in the en face view.

Additional disclosed embodiments include an OCT scanner, a surgical microscope, and an image processing system.

BRIEF DESCRIPTION OF THE DRAWINGS

For a more complete understanding of the present disclosure, reference is now made to the following description, taken in conjunction with the accompanying drawings, in which.

DESCRIPTION OF PARTICULAR EMBODIMENTS

Figure 1:
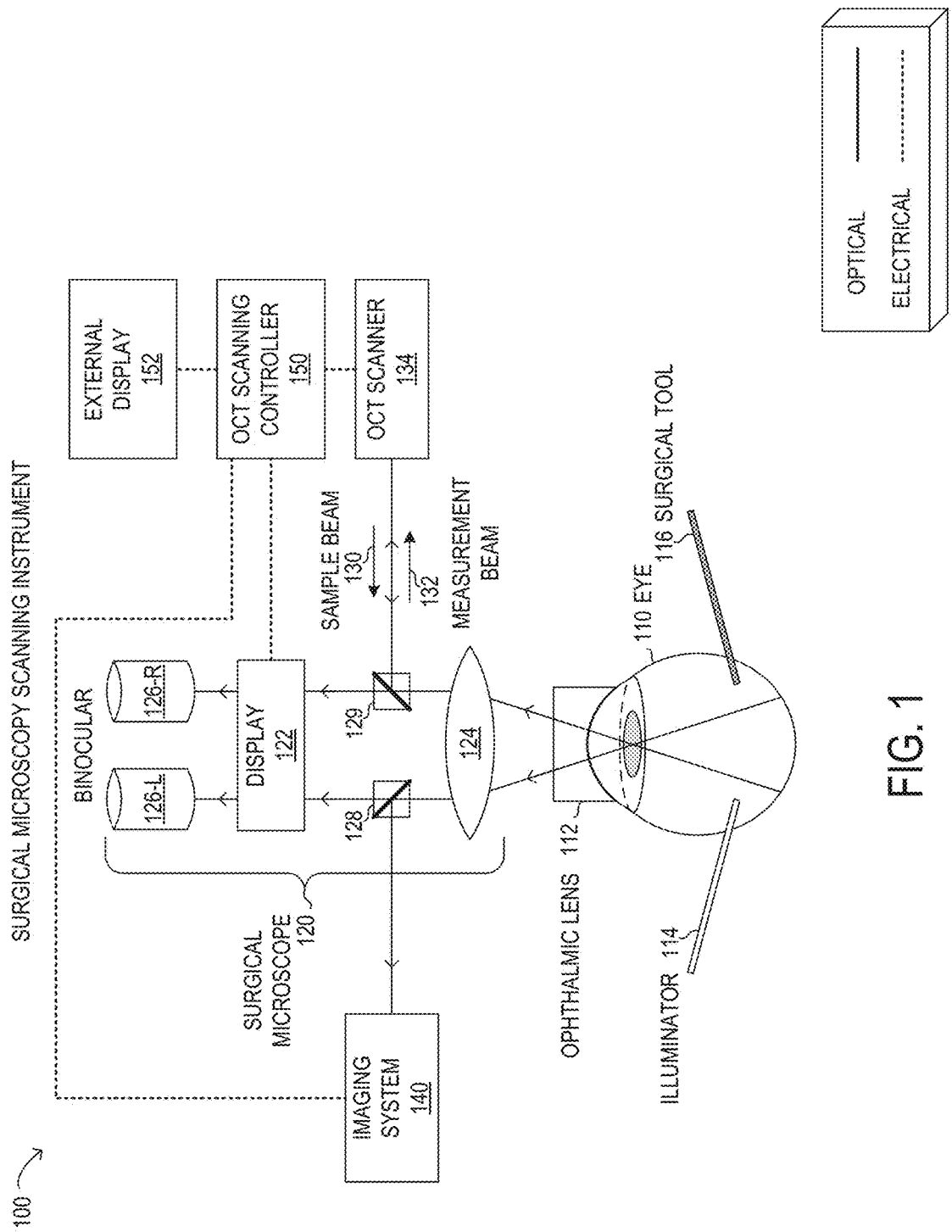
FIG. 1 is a block diagram of selected elements of an embodiment of a surgical microscopy scanning instrument.

In the following description, details are set forth by way of example to facilitate discussion of the disclosed subject matter. It should be apparent to a person of ordinary skill in the field, however, that the disclosed embodiments are exemplary and not exhaustive of all possible embodiments.

As used herein, a hyphenated form of a reference numeral refers to a specific instance of an element and the un-hyphenated form of the reference numeral refers to the collective element. Thus, for example, device '12-1' refers to an instance of a device class, which may be referred to collectively as devices '12' and any one of which may be referred to generically as a device '12'.

As noted above, during vitreoretinal surgery a surgeon may view the fundus of an eye of a patient using a surgical microscope, for example, in conjunction with an ophthalmic lens for viewing through the cornea, such as a contact or non-contact lens. In order to perform any of a variety of surgical procedures, the surgeon may desire to optically scan certain portions of the fundus to generate profile depth scans of the corresponding eye tissue, such as by using an OCT scanner. The profile depth scans may reveal information about eye tissue that is not readily visible from optical images generated by the surgical microscope. The profile depth scans may be point scans (A-scan), line scans (B-scan), or area scans (C-scan). An image from a B-scan will image the depth of eye tissue along a line, while a C-scan results in 3-dimensional (3D) data that can be sectioned to provide various views, including an en face view from the optical view perspective, but which can be generated at various depths and for selected tissue layers.

Although OCT scanners have been integrated with the optics of surgical microscopes, the imagery that can be provided using OCT may be different in certain aspects than the optical images that the surgeon views intraoperatively. For example, because of the optical properties of various ophthalmic lenses used to image interior portions of the eye, the curvature of field of the optical images may be substantially different than OCT images acquired for the same tissue. Such disparities in the curvature of field may create difficulties for the surgeon to adapt to the differing views. While the human brain is adept at adapting to a given visual distortion, adapting to two different curvatures of field for the same image is more difficult and potentially prone to errors, such as errors in perceiving a depth of eye tissue, which can be crucial during surgery. In particular, en face OCT imaging will experience the most significant distortions due to disparate curvature of field as compared to the optical image.

The present disclosure relates to curvature of field transformation of OCT images during vitreoretinal surgery. The methods and systems for curvature of field transformation of OCT images during vitreoretinal surgery disclosed herein may enable the surgeon to view en face OCT images that are corrected to match a curvature of field of the optical image viewed by the surgeon using the surgical microscope.

As will be described in further detail, curvature of field transformation of OCT images during vitreoretinal surgery disclosed herein is performed using an OCT scanning controller that is integrated with the OCT scanner and the surgical microscope. The OCT scanning controller may send commands to control operation of the OCT scanner, including for positioning as indicated by a user, typically the surgeon. The OCT scanning controller may receive user input and may communicate with the OCT scanner to acquire first scan data that is usable to generate an en face view of an interior of an eye of a patient. The OCT scanning controller may apply an anamorphic transformation to the first scan data to generate second scan data that matches a curvature of field of the optical image.

Referring now to the drawings, FIG. 1 is a block diagram showing a surgical microscopy scanning instrument 100. Instrument 100 is not drawn to scale but is a schematic representation. As will be described in further detail, instrument 100 may be used during vitreoretinal surgery to view and analyze a human eye 110. As shown, instrument 100 includes surgical microscope 120, OCT scanning controller 150, external display 152, and OCT scanner 134. Also shown in FIG. 1 are imaging system 140, ophthalmic lens 112, as well as surgical tool 116 and illuminator 114.

As shown, surgical microscope 120 is depicted in schematic form to illustrate optical functionality. It will be understood that surgical microscope 120 may include various other electronic and mechanical components, in different embodiments. Accordingly, objective 124 may represent a selectable objective to provide a desired magnification or field of view of the fundus. Objective 124 may receive light from the fundus of eye 110 via ophthalmic lens 112 that rests on a cornea of eye 110. It is noted that various types of ophthalmic lenses 112 may be used with surgical microscope 120, including contact lenses and non-contact lenses. To perform vitreoretinal surgery, various tools and instruments may be used, including tools that penetrate the sclera, represented by surgical tool 116. Illuminator 114 may be a special tool that provides a light source from within the fundus of eye 110.

In FIG. 1, surgical microscope 120 is shown with a binocular arrangement with two distinct but substantially equal light paths that enable viewing with binoculars 126 that comprise a left ocular 126-L and a right ocular 126-R. From objective 124, a left light beam may be split at beam splitter 128, from where imaging system 140 and left ocular 126-L receive the optical image. Also from objective 124, a right light beam may be split at partial mirror 129, which also receives sample beam 130 from OCT scanner 134, and outputs measurement beam 132 to OCT scanner 134. Partial mirror 129 also directs a portion of the right light beam to right ocular 126-R. Display 122 may represent an optoelectronic component, such as an image processing system that receives the data from OCT scanning controller 150 and generates image output for left ocular 126-L and right ocular 126-R, respectively. In some embodiments, display 122 includes miniature display devices that output images to binoculars 126 for viewing by the user. It is noted that the optical arrangement depicted in FIG. 1 is exemplary and may be implemented differently in other embodiments.

In FIG. 1, OCT scanning controller 150 may have an electrical interface with display 122, for example, for outputting display data. In this manner, OCT scanning controller 150 may output a display image to display 122 that is viewed at binoculars 126. Because the electrical interface between imaging system 140 and OCT scanning controller 150 may support digital image data, OCT scanning controller 150 may perform image processing in real-time with relatively high frame refresh rates, such that a user of surgical microscope 120 may experience substantially instantaneous feedback to user input for controlling the selected portion of eye 110 for scanning, as well as other operations. External display 152 may output similar images as display 122, but may represent a stand-alone monitor for viewing by various personnel during vitreoretinal surgery. Display 122 or external display 152 may be implemented as a liquid crystal display screen, a computer monitor, a television or the like. Display 122 or external display 152 may comply with a display standard for the corresponding type of display, such as video graphics array (VGA), extended graphics array (XGA), digital visual interface (DVI), high-definition multimedia interface (HDMI), etc.

With the binocular arrangement of surgical microscope 120 in FIG. 1, imaging system 140 may receive a portion of the left light beam that enables imaging system 140 to independently process, display, store, and otherwise manipulate light beams and image data. Accordingly, imaging system 140 may represent any of a variety of different kinds of imaging systems, as desired.

As shown, OCT scanner 134 may represent an embodiment of various kinds of OCT scanners. It is noted that other types of optical scanners may be used with the arrangement depicted in FIG. 1. OCT scanner 134 may control output of sample beam 130 and may receive measurement beam 132 that is reflected back in response to photons of sample beam 130 interacting with tissue in eye 110. OCT scanner 134 may also be enabled to move sample beam 130 to the selected location indicated by the user. OCT scanning controller 150 may interface with OCT scanner 134, for example, to send commands to OCT scanner 134 indicating the selected location to generate scan data, and to receive the scan data from OCT scanner 134. It is noted that OCT scanner 134 may represent various types of OCT instruments and configurations, as desired, such as but not limited to time domain OCT (TD-OCT) and frequency domain OCT (FD-OCT). In particular, the scan data generated by OCT scanner 134 may include two-dimensional (2D) scan data of a line scan and three-dimensional (3D) scan data for an area scan. The scan data may represent a depth profile of the scanned tissue that enables imaging below a visible surface within the fundus of eye 110.

In operation of instrument 100, the user may view the fundus of eye 110 using binoculars while vitreoretinal surgery is performed on eye 110. The user may provide user input to OCT scanning controller 150 to initiate an OCT scan. OCT scanning controller 150 may, in turn, communicate with OCT scanner 134 to control scanning operations and perform a real-time OCT scan to generate first scan data. However, the first scan data generated by OCT scanner 134 intraoperatively may not match a curvature of field of the optical image viewed, as discussed previously. Therefore, instead of displaying the first scan data at display 122, OCT scanning controller 150 may apply an anamorphic transformation to the first scan data to generate second scan data matching the curvature of field. The anamorphic transformation may be an affine transform, or another type of transform. Various methods may be used to determine parameters for the anamorphic transformation. In one embodiment, optical properties of instrument 100, such as known anamorphic distortion of objective 124 or ophthalmic lens 112, among other optical components, may be determined and used for the anamorphic transformation. In some embodiments, certain tissue features in the optical image, such as retinal blood vessels, may be used to align corresponding tissue features in the first scan data (the raw OCT image) or to determine parameters of the anamorphic transformation being applied.

Modifications, additions, or omissions may be made to surgical microscopy scanning instrument 100 without departing from the scope of the disclosure. The components and elements of surgical microscopy scanning instrument 100, as described herein, may be integrated or separated according to particular applications. Surgical microscopy scanning instrument 100 may be implemented using more, fewer, or different components in some embodiments.

Figure 2:
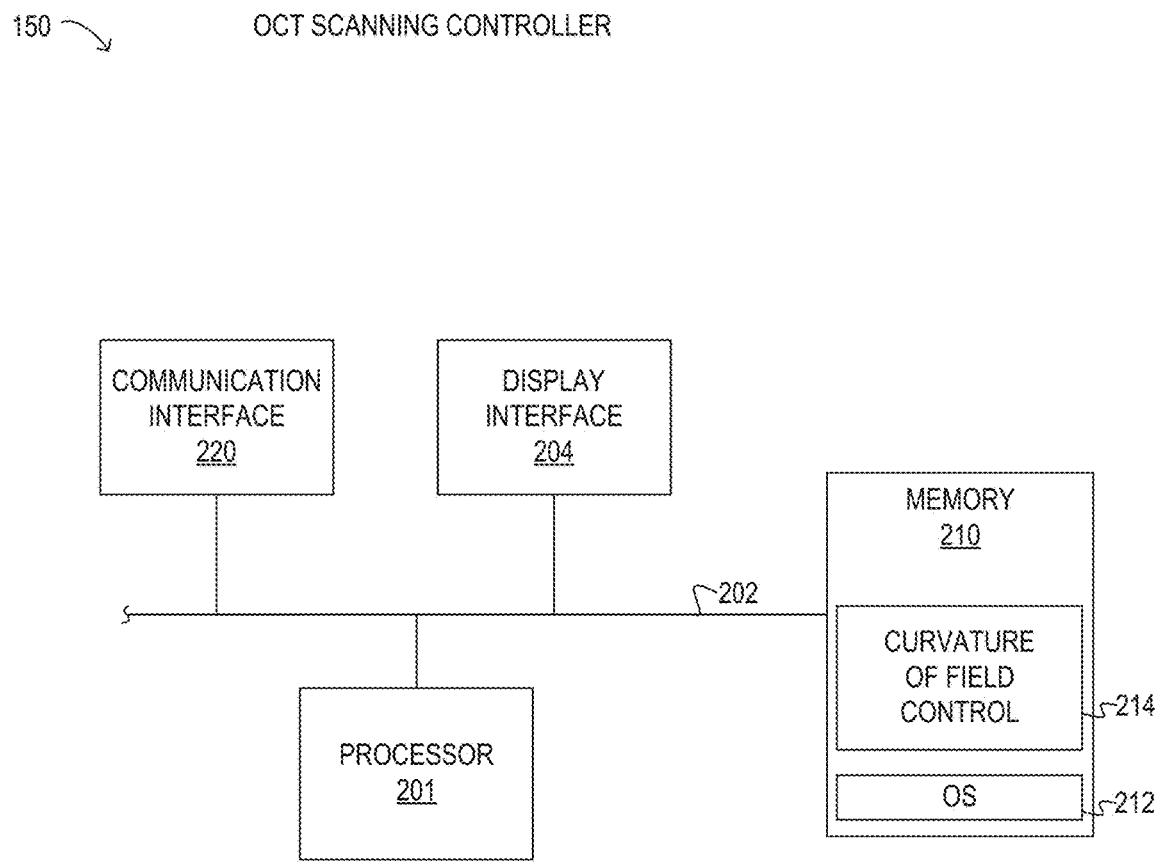
FIG. 2 is a block diagram of selected elements of an embodiment of a scanning controller.

Referring now to FIG. 2, a block diagram illustrating selected elements of an embodiment of OCT scanning controller 150, described above with respect to FIG. 1, is presented. In the embodiment depicted in FIG. 2, OCT scanning controller 150 includes processor 201 coupled via shared bus 202 to memory media collectively identified as memory 210.

OCT scanning controller 150, as depicted in FIG. 2, further includes communication interface 220 that can interface OCT scanning controller 150 to various external entities, such as OCT scanner 134 or imaging system 140, among other devices. In some embodiments, communication interface 220 is operable to enable OCT scanning controller 150 to connect to a network (not shown in FIG. 2). In embodiments suitable for resolution enhancement of OCT images during vitreoretinal surgery, OCT scanning controller 150, as depicted in FIG. 2, includes display interface 204 that connects shared bus 202, or another bus, with an output port for one or more displays, such as display 122 or external display 152.

In FIG. 2, memory 210 encompasses persistent and volatile media, fixed and removable media, and magnetic and semiconductor media. Memory 210 is operable to store instructions, data, or both. Memory 210 as shown includes sets or sequences of instructions, namely, an operating system 212, and a curvature of field control application 214. Operating system 212 may be a UNIX or UNIX-like operating system, a Windows® family operating system, or another suitable operating system.

Figure 3:
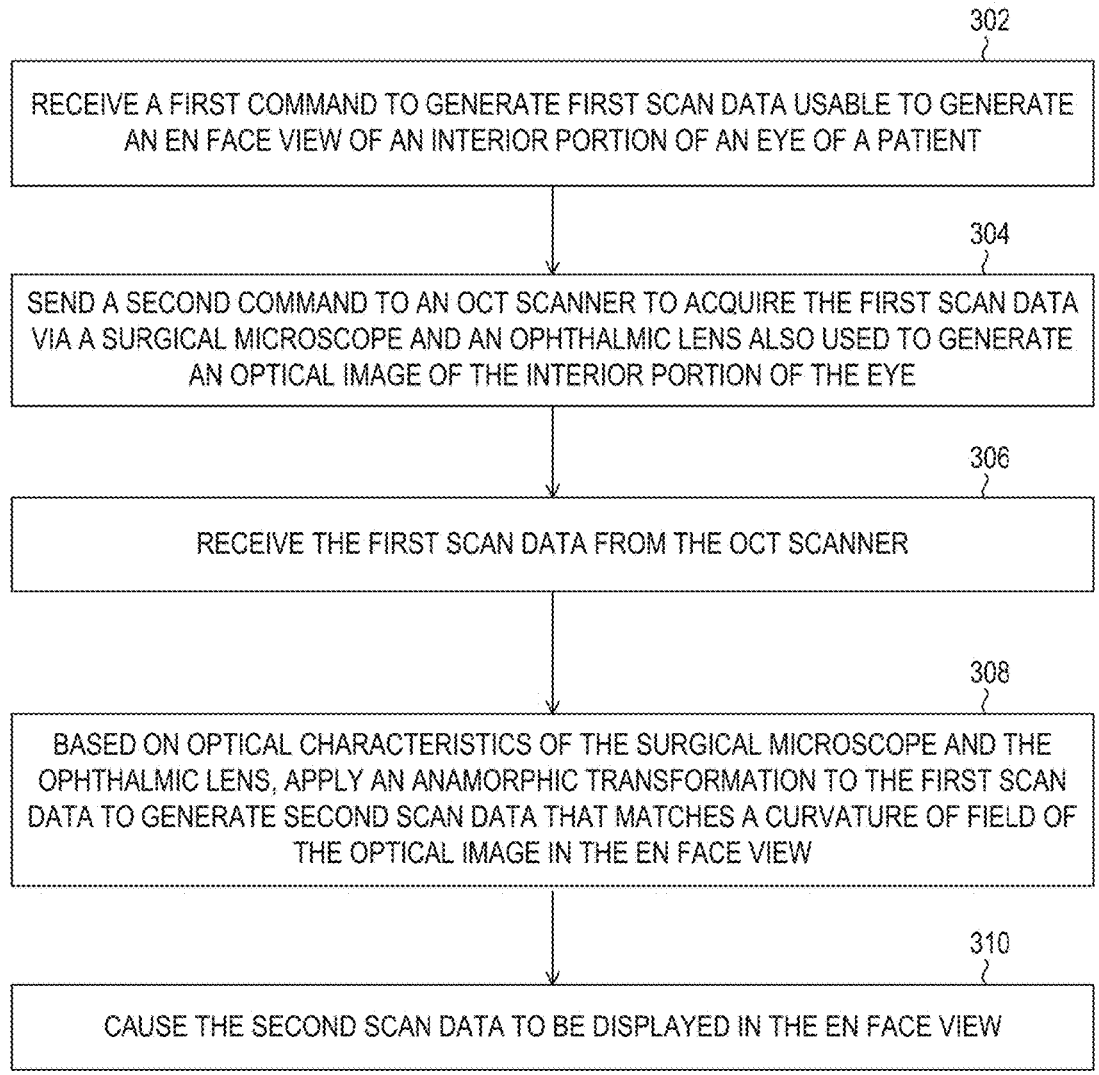
FIG. 3 is a flow chart of selected elements of a method for curvature of field transformation of OCT images during vitreoretinal surgery.

Referring now to FIG. 3, a flow chart of selected elements of an embodiment of a method 300 for curvature of field transformation of OCT images during vitreoretinal surgery, as described herein, is depicted in flowchart form. Method 300 describes steps and procedures that may be performed while surgical microscopy scanning instrument 100 is operated to view the fundus of an eye and perform surgical procedures based on the view of the fundus. Accordingly, at least certain portions of method 300 may be performed by curvature of field control application 214. It is noted that certain operations described in method 300 may be optional or may be rearranged in different embodiments. Method 300 may be performed by curvature of field control application 214 to interact with a surgeon or other medical personnel, referred to herein as a "user".

Prior to method 300, it may be assumed that surgical microscopy scanning instrument 100 is being used to view an interior portion of an eye of a patient, such as described in FIG. 1. Then, method 300 may begin, at step 302, by receiving a first command to generate first scan data usable to generate an en face view of the interior portion of the eye. The first scan data are C-scans (volumetric scans) of the interior portion of the eye. At step 304, a second command is sent to an OCT scanner to acquire the first scan data via the surgical microscope and an ophthalmic lens also used to generate an optical image of the interior portion of the eye. At step 306, the first scan data may be received from the OCT scanner. At step 308, based on optical characteristics of the surgical microscope and the ophthalmic lens, an anamorphic transformation may be applied to the first scan data to generate second scan data that matches a curvature of field of the optical image in the en face view. The second scan data are also C-scans (volumetric scans) of the interior portion of the eye. Additionally, it is noted that the anamorphic transformation in step 308 is dependent on a number of variables and factors associated with instrument 100. For example, the anamorphic transformation is dependent on a microscope magnification or selection of a given objective 124, as well as on a type of ophthalmic lens 112 used. The anamorphic transformation may also be dependent on a distance between an optical element, such as a non-contact lens used for ophthalmic lens 112, and the eye. Thus, upon a change in such operative variables, at least step 308 in method 300 may be repeated to refresh the second scan data.

At step 310, the second scan data may be caused to be displayed in the en face view. It is noted that the second scan data are displayed in addition to the optical image provided by the surgical microscope that is a live optical view of the interior portion of the eye. Various other OCT operations on the en face view of the second scan data may be performed, such as selection of certain depths or depth ranges for viewing. In some embodiments, the OCT scanning controller may be enabled to image only desired tissue layers in the en face view of the second scan data, responsive to an indication by the user to select the desired tissue layers. The second scan data may be displayed in the en face view at binoculars 126 or at external display 152 or both.

As disclosed herein, curvature of field transformation of OCT images during ophthalmic surgery may be performed with an OCT scanning controller that interfaces to an OCT scanner used with a surgical microscope. Real-time OCT images may be acquired by the OCT scanner, while an anamorphic transformation is applied to the OCT images to match the curvature of field for optical images viewed using the surgical microscope. The transformed OCT images may be displayed during surgery.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method for performing ophthalmic surgery, the method comprising:
    viewing an interior portion of an eye of a patient using a surgical microscope and an ophthalmic lens generating an optical image of the interior portion of the eye;
    sending a command to an optical coherence tomography (OCT) scanning controller coupled to the surgical microscope to generate first scan data from the interior portion of the eye, wherein the OCT scanning controller is in communication with an OCT scanner enabled for acquiring the first scan data, wherein the OCT scanning controller is enabled for,
        receiving the first scan data from the OCT scanner, wherein the first scan data are usable to generate an en face view of the interior portion of the eye;
        based on optical characteristics of the surgical microscope and the ophthalmic lens, applying an anamorphic transformation to the first scan data to generate second scan data that matches a curvature of field of the optical image in the en face view; and
        causing the second scan data to be displayed in the en face view.

2. The method of claim 1, wherein the second scan data are displayed in an ocular of the surgical microscope.

3. The method of claim 1, wherein the second scan data are displayed in an external display.

4. The method of claim 1, wherein the first scan data are received as a video signal, and the second scan data are displayed as a video signal.

5. The method of claim 1, wherein applying the anamorphic transformation further comprises:
    aligning first tissue features in the first scan data with corresponding second tissue features in the optical image to determine the curvature of field.

6. The method of claim 5, wherein the first tissue features and the second tissue features include retinal blood vessels.

7. The method of claim 1, wherein the optical characteristics include anamorphic distortion of an objective lens included in the surgical microscope.

8. The method of claim 1, wherein the optical characteristics include anamorphic distortion of the ophthalmic lens.

9. The method of claim 1, further comprising:
    receiving an indication of desired tissue layers captured in the first scan data; and
    generating the second scan data to image only the desired tissue layers in the en face view.

10. An optical coherence tomography (OCT) scanning controller to perform curvature of field transformation of OCT images during ophthalmic surgery, the OCT scanning controller further comprising:
   a processor having access to memory media storing instructions executable by the processor for, receiving a first command to generate first scan data from an interior portion of an eye of a patient;
   sending a second command to an OCT scanner to acquire the first scan data via a surgical microscope and an ophthalmic lens, wherein the surgical microscope and the ophthalmic lens are also used to generate an optical image of the interior portion of the eye;
   receiving the first scan data from the OCT scanner, wherein the first scan data are usable to generate an en face view of the interior portion of the eye;
   based on optical characteristics of the surgical microscope and the ophthalmic lens, applying an anamorphic transformation to the first scan data to generate second scan data that matches a curvature of field of the optical image in the en face view; and
   causing the second scan data to be displayed in the en face view.

11. The OCT scanning controller of claim 10, wherein the instructions for causing the second scan data to be displayed in the en face view include instructions for causing the second scan data to be displayed in an ocular of the surgical microscope.

12. The OCT scanning controller of claim 10, wherein the instructions for causing the second scan data to be displayed in the en face view include instructions for causing the second scan data to be displayed in an external display.

13. The OCT scanning controller of claim 10, wherein the first scan data are received as a video signal, and the second scan data are displayed as a video signal.

14. The OCT scanning controller of claim 10, wherein the instructions for applying the anamorphic transformation further comprise instructions for:
   aligning first tissue features in the first scan data with corresponding second tissue features in the optical image to determine the curvature of field.

15. The OCT scanning controller of claim 14, wherein the first tissue features and the second tissue features include retinal blood vessels.

16. The OCT scanning controller of claim 10, wherein the optical characteristics include anamorphic distortion of an objective lens included in the surgical microscope.

17. The OCT scanning controller of claim 10, wherein the optical characteristics include anamorphic distortion of the ophthalmic lens.

18. The OCT scanning controller of claim 10, further comprising instructions for:
   receiving an indication of desired tissue layers captured in the first scan data; and
   generating the second scan data to image only the desired tissue layers in the en face view.

* * * * *